United States Patent [19]

Maeda et al.

[11] 4,095,973
[45] Jun. 20, 1978

[54] COMPOSITION FOR INCREASING YIELD OF PULSE

[75] Inventors: Seiichi Maeda, Wakayama; Kan Mori, Kawasaki; Tsuneyuki Takeno, Wakayama, all of Japan

[73] Assignee: Kao Soap Co., Ltd., Tokyo, Japan

[21] Appl. No.: 737,780

[22] Filed: Nov. 1, 1976

[30] Foreign Application Priority Data

Nov. 6, 1975 Japan .................. 50-133290

[51] Int. Cl.² .............................. A01N 9/14
[52] U.S. Cl. ............................ 71/103; 71/76; 71/92; 71/106; 71/122; 71/124; 71/127; 71/DIG. 1
[58] Field of Search ............. 71/103, 76; 260/513 R

[56] References Cited

U.S. PATENT DOCUMENTS

| | | | |
|---|---|---|---|
| 2,613,218 | 10/1952 | Stoneman | 260/513 R |
| 2,678,878 | 5/1954 | Stewart | 71/103 |
| 2,802,027 | 8/1967 | Gaertner | 71/103 |
| 3,978,228 | 8/1976 | Yoshinaga et al. | 71/103 |

OTHER PUBLICATIONS

Societe Anon., "Compositions for Stimulation, etc." (1971), CA. 76, No. 82193w, (1972).
Veldstra et al., "Structure–Activity, etc.," (1954), CA 48, pp. 6515–6516, (1954).

*Primary Examiner*—Glennon H. Hollrah
*Attorney, Agent, or Firm*—Oblon, Fisher, Spivak, McClelland & Maier

[57] ABSTRACT

A composition which increases the yield of pulse, comprising an effective amount of at least one component selected from the group consisting of a sulfonate represented by the formula $$R^1-SO_3M,$$

wherein $R^1$ represents alkyl or alkenyl of 8 to 20 carbon atoms or the residue of succinic acid esters represented by the formula, $$\begin{array}{c} CH_2-COOR^2 \\ | \\ -CH-COOR^3 \end{array}$$

wherein $R^2$ and $R^3$ represent alkyl of 1 to 18 carbon atoms or alkylaryl containing an alkyl group of 1 to 18 carbon atoms and M represents an organic or inorganic cation; and a sulfuric ester represented by the formula $$R^4-O-SO_3M,$$

wherein $R^4$ represents an alkyl group having 8 to 20 carbon atoms or an alkylaryl group containing an alkyl group of 8 to 20 carbon atoms and M is the same as defined above.

5 Claims, No Drawings

COMPOSITION FOR INCREASING YIELD OF PULSE

The present invention relates to a composition suitable for increasing the yield of pulse.

Accordingly, a primary object of the present invention is to provide a composition suitable for increasing the yield of pulse by causing the removal of abortive flowers and for controlling the over-growth of stems and leaves. Generally, pulse abounds in more abortive flowers than fructification. Accordingly, an increased yield and improvement in the quality of pulse should be expected when abortive flowers are removed to appropriate assimilated products via photosynthesis for fructification and enlargement of seed. In the bulb culturing of Lilium longiflorum, flowers and buds have been removed in order to fatten the bulbs.

However, it has been reported that the picking of abortive flowers from peanuts plants by hand causes a significant decrease in the weight of seeds thereby resulting in low harvests [NISSAKUKI (summary), 34, 493 1966)]. This fact suggests that the picking of only abortive flowers by hand stimulates an increase in the amount of nutrient flowing to the stems and leaves of the plant resulting in overgrowth on the ground.

In the past compounds have been investigated for the removal of flowers, buds or fruits, and as a result, various compounds have been developed, such as the diethanolamine salt of maleic acid hydrazide, which has been put to practical use as an axillary bud inhibitor, and alkylbenzenesulfonate derivatives, which have been reported to be effective in the picking of lily buds (publication number 1531/1874).

A wide variety of chemicals have been investigated in order to increase the yield of pulse. In the specific situation of the peanut taken as an example of pulse, its vegetative growth proceeds simultaneously with reproductive growth after germination, and the flowering period is very long, depending upon the variety of peanuts, environmental conditions and cultivation methods. The peanut flowers continuously from the beginning of July to the middle of September. The number of effective flowers is about 40 to 50 in the early flowering period of the plant.

After autogamy, the gynophores penetrate into the soil to form pods, and the seed enlarges. The maturing period of an ovary is about 90 days. In the case where flowering starts at about the beginning of July, the seeds do not mature by harvest, although flowers after August extend the gynophores after pollination. Accordingly, these late flowers assimilate material which could be used by the plant in the bearing of fruit which detrimentally affects the yield and quality of fruit from the plant.

In the study leading to the present invention a wide variety of chemicals capable of controlling the unnecessary extension of stems and leaves in plants as well as facilitating the removal of abortive flowers and buds were investigated. As a result of the study, it was found that sulfonates (I) or sulfuric esters (II) having the following formulas achieve the objectives of the present invention.

 (I)

 (II)

In the formulas $R^1$ represents alkyl or alkenyl having 8 to 20 carbon atoms or the residue of succinic acid esters having the formula,

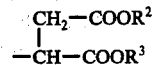

wherein $R^2$ and $R^3$ represent alkyl of 1 to 18 carbon atoms or alkylaryl containing an alkyl group of 1 to 18 carbon atoms; $R^4$ represents alkyl of 8 to 20 carbon atoms or alkylaryl containing an alkyl group of 8 to 20 carbon atoms; and M represents an organic or inorganic cation. Furthermore, it has been found that the addition of non-ionic surface active agents to the above sulfonates of formula (I) or sulfuric esters of formula (II) further enhance the effects of these compounds. Accordingly, the present invention provides a composition which increases the yield of pulse. The composition comprises, as effective ingredients, at least one component of a sulfonate of formula (I) or a sulfuric ester of formula (II). Another embodiment of the present composition which results in increased yield of pulse is formed by mixing at least one non-ionic surface active agent with the above composition.

The cations represented by M in formulas (I) and (II) include inorganic cations such as potassium, sodium and calcium, and organic cations such as monoethanolammonium, diethanolammonium and isopropylammonium.

Suitable sulfonates of formula (I) include sodium α-olefin (C13) sulfonate, sodium dodecylsulfonate, isopropylammonium dodecylsulfonate, sodium dioctylsulfosuccinate, and sodium 2-ethylhexyl-sulfosuccinate.

Suitable sulfuric esters of formula (II) include sodium laurylsulfate and sodium octylsulfate.

Suitable non-ionic surface active agents include polyoxyethylene fatty acid ester, polyoxyethylene sorbitan fatty acid ester, polyoxyethylene alkyl ether, polyoxyethylene alkylaryl ether, polyoxyethylene castor oil ether wherein the number of moles of the added ethylene oxide units is preferably 5 to 20 and the alkyl groups preferably contain from 4 to 20 carbon atoms, fatty acid mono- and di-glycerides, ethylene oxide-propylene oxide block polymers, sucrose fatty acid esters, sorbitan fatty acid esters and sorbitol fatty acid esters wherein the alkyl groups preferably contain 4 to 20 carbon atoms.

The present sulfonate or sulfuric ester composition or the embodiment of the composition containing a non-ionic surface active agent mixed with a sulfonate or sulfuric ester should be diluted with a suitable diluent so that the non-solvent constituents of the diluted solution should be in the range of 0.01 to 10 percent by weight, preferably 0.3 to 5 percent by weight, in order to be practically useful. The ratio of the amount of non-ionic surface active agent to the sulfonate or sulfuric ester component should be in the range of 0.1 to 0.5 part by weight based on one part by weight of the sulfonate or sulfuric ester. If the content of the effective ingredients in the solution is less than 0.01 percent by weight, the desired flower removal effect cannot be expected. If the effective ingredient content thereof is over 10 percent by weight, the diluted chemicals may exert harmful effects on the treated crops.

The above ingredients may be used alone or in combination with suitable fillers. The present composition can be used in various forms such as a powder, a wettable powder, an aqueous solution, an emulsifiable concentrate, or an oil spray which are all useful forms of common agricultural chemicals.

Suitable fillers useful in the present invention include clay, kaolin, bentonite, terra abla, diatomaceous earth, calcium carbonate, methyl cellulose, starch, gum arabi, water, ethanol, propanol, butanol, isobutanol, octanol, glycols, methyl caprate, acetone, benzene, xylene, carbonic acid gas and freon gas. Of the above fillers, alcohols such as propanol, butanol and octanol, hydrocarbons such as xylene and fatty acid esters such as methyl caprate, potentiate the effects of the above presented combination of ingredients.

The present composition can be applied to plants by spraying, preferably once or twice at a time of 20 to 25 days after flowering at intervals of 10 to 15 days.

In order that the composition may uniformly adhere to the whole stubs of a plant, the spray volume should range from 20 to 25 liters per 100 m$^2$, this ratio of application controls flowering very well and affords an increased yield of pulse.

Having generally described the invention, a more complete understanding can be obtained by reference to certain specific examples, which are included for purposes of illustration only and are not intended to be limiting unless otherwise specified.

EXAMPLE 1

Aqueous Solution

Forty percent aqueous solution of sodium α-olefin (C13) sulfonate. Before use this solution was diluted 100 times with water.

EXAMPLE 2

Aqueous Solution

A seventy percent methanol solution of sodium 2-ethylhexylsulfosuccinate. Before use, this solution was diluted 200 times with water.

EXAMPLE 3

Aqueous Solution

Polyoxyethylene (20) sorbitan monooleate was added to a 40% aqueous solution of sodium α-olefin (C13) sulfonate to form a 10% solution of polyoxyethylene (20) sorbitan Monooleate. Before use this solution was diluted 100 times with water.

EXAMPLE 4

A variety of peanut known as Chibahandachi was seeded on the 12th of May in a field, which was composted with a mixture of 100 Kg of compost, 20 kg of dolomite, 0.3 Kg of N, 1.0 Kg of $P_2O_5$ and 1.0 Kg of $K_2O$ per 100 m$^2$. The field was divided into two sections each having an area of 4.2 m$^2$, and twenty stubs of peanut were planted in each section 30 cm apart in each row. The distance between rows was 70 cm.

On the 1st of August which fell on the 25th day after initial flowering, a test composition diluted with water was sprayed on the whole plant at a rate of 25 liters per 100 m$^2$ by a handsprayer.

Any plant damage from the test composition was observed with the naked eye on the 40th day after the treatment, and the number and the weight of well-developed seeds as well as the number and the weight of well-developed pods were measured at the time of harvest.

The results are as shown in the following table. The test Compounds having numbers 1 to 10 represent compositions of the present invention and numbers 20 to 24 represent control compositions.

| | Test compounds | Concentration (%) | Harvest (per plant) | | | | Harmful effects of chemicals |
|---|---|---|---|---|---|---|---|
| | | | Number of well-developed pods | Weight of well-developed pods | Number of well-developed seeds | Weight of well-developed seeds | |
| 1 | sodium α-olefin (C13) sulfonate | 0.5 | 25.8 | 39.1 | 37.6 | 24.6 | — |
| 2 | sodium α-olefin (C13) sulfonate | 1.0 | 26.5 | 40.2 | 38.5 | 25.2 | — |
| 3 | sodium α-olefin (C13) sulfonate | 2.0 | 26.6 | 40.5 | 38.7 | 25.8 | — |
| 4 | calcium α-olefin (C13) sulfonate | 0.5 | 26.0 | 38.9 | 37.5 | 24.5 | — |
| 5 | sodium laurylsulfate | 0.5 | 26.0 | 39.0 | 37.5 | 24.5 | — |
| 6 | sodium dodecylsulfonate | 0.5 | 26.3 | 39.2 | 37.4 | 24.8 | — |
| 7 | sodium dodecylsulfonate | 1.0 | 26.4 | 41.0 | 38.8 | 25.5 | — |
| 8 | sodium dodecylsulfonate | 3.0 | 26.8 | 41.2 | 38.9 | 25.6 | ± |
| 9 | sodium 2-ethylhexylsulfosuccinate | 0.3 | 26.0 | 39.0 | 37.8 | 24.8 | — |
| 10 | sodium isobutylsulfosuccinate | 0.3 | 26.1 | 39.2 | 38.3 | 24.8 | — |
| 11 | sodium α-olefin (C13) sulfonate<br>polyoxyethylene (20) sorbitan monooleate | 0.4<br>0.1 | 26.2 | 39.8 | 38.0 | 25.2 | — |
| 12 | sodium α-olefin (C13) sulfonate<br>polyoxyethylene (6) lauryl ether | 0.4<br>0.1 | 26.1 | 39.7 | 37.9 | 25.0 | — |
| 13 | sodium α-olefin (C13) sulfonate<br>polyoxyethylene (10) nonylphenol ether | 0.3<br>0.2 | 26.2 | 39.5 | 37.8 | 25.1 | — |
| 14 | sodium laurylsulfate<br>polyoxyethylene (6) lauryl ether | 0.3<br>0.2 | 26.2 | 39.3 | 37.8 | 25.0 | — |
| 15 | sodium dodecylsulfonate<br>polyoxyethylene (20) sorbitan monooleate | 0.4<br>0.1 | 26.5 | 39.3 | 37.8 | 24.8 | — |
| 16 | sodium dodecylsulfonate<br>polyoxyethylene (6) lauryl ether | 0.4<br>0.1 | 26.5 | 39.4 | 38.0 | 25.0 | — |
| 17 | sodium dodecylsulfonate<br>polyoxyethylene (10) nonylphenol ether | 0.3<br>0.2 | 26.6 | 39.8 | 38.2 | 25.2 | — |
| 18 | sodium 2-ethylhexylsulfosuccinate | 0.1 | 26.5 | 39.4 | 38.0 | 25.0 | — |

-continued

| | Test compounds | Concentration (%) | Harvest (per plant) | | | | Harmful effects of chemicals |
| --- | --- | --- | --- | --- | --- | --- | --- |
| | | | Number of well-developed pods | Weight of well-developed pods | Number of well-developed seeds | Weight of well-developed seeds | |
| | polyoxyethylene (20) sorbitan monooleate | 0.2 | | | | | |
| 19 | sodium isobutylsulfosuccinate | 0.1 | 26.5 | 39.4 | 38.3 | 25.2 | — |
| | polyoxyethylene (20) sorbitan monooleate | 0.2 | | | | | |
| 20 | sodium dodecylbenzenesulfonate | 19.8 | 29.8 | 29.5 | 17.5 | ± |  |
| 21 | calcium dodecylbenzenesulfonate | 0.5 | 19.4 | 29.7 | 29.5 | 17.4 | ± |
| 22 | polyoxyethylene (20) sorbitan monooleate | 0.5 | 18.4 | 28.0 | 27.8 | 18.0 | — |
| 23 | polyoxyethylene (6) lauryl ether | 0.5 | 18.0 | 27.9 | 27.5 | 18.1 | + |
| 24 | polyoxyethylene (10) nonylphenol ether | 0.5 | 18.1 | 27.5 | 27.8 | 17.5 | + |
| 25 | untreated | — | 20.5 | 30.1 | 29.6 | 18.9 | — |

Having now fully described the invention, it will be apparent to one of ordinary skill in the art that many changes and modifications can be made thereto without departing from the spirit or scope of the invention as set forth herein.

What is claimed as new and intended to be secured by letters patent is:

1. A method of increasing the yield of peanuts which comprises applying thereto an effective amount of the composition which comprises from 0.01 to 10 wt. percent of an admixture of a sulfonate of the formula:

$R^1SO_3M$ wherein $R^1$ is an alkyl or alkenyl group having 8 to 20 carbon atoms and M is selected from the group consisting of potassium, sodium, calcium, monoethanolammonium, and diethanolammonium; 0.1 to 0.5 wt. parts of a nonionic surface-active agent per weight part of said sulfonate and an inert diluent.

2. The method of claim 1, wherein said non-ionic surfactant is selected from the group consisting of polyoxyethylene fatty acid ester, polyoxyethylene sorbitan fatty acid ester, polyoxyethylene alkyl ether, polyoxyethylene alkylaryl ether, polyoxyethylene castor oil ether wherein the number of moles of the added ethylene oxide units is 5 to 20 and the alkyl groups contain from 40 to 20 carbon atoms, fatty acid mono- and diglycerides, ethylene oxide-propylene oxide block polymers, sucrose fatty acids esters, sorbitan fatty acid esters and sorbitol fatty acid ester wherein the alkyl groups contain 4 to 20 carbon atoms.

3. The method of claim 1, wherein said sulfonate is selected from the group consisting of α-olefin (C13)-sulfonate and dodecylsulfonate.

4. A method of increasing the yield of peanuts which comprises applying thereto an effective amount of the composition which comprises from 0.01 to 10 wt. percent of a sulfonate of the formula $R^1SO_3M$ wherein $R^1$ is an alkyl or alkenyl group having 8 to 20 carbon atoms and M is selected from the group consisting of potassium, sodium, calcium, monoethanolammonium, and diethanolammonium; and an inert diluent.

5. The method of claim 4, wherein the sulfonate is selected from the group consisting of α-olefin (C13)-sulfonate and dodecylsulfonate.

* * * * *